United States Patent
Buddha et al.

(10) Patent No.: US 10,611,813 B2
(45) Date of Patent: Apr. 7, 2020

(54) METHOD OF PRODUCTION OF HUMAN INSULIN METHYL ESTER

(71) Applicant: BIOCON RESEARCH LIMITED, Bangalore (IN)

(72) Inventors: Madhavan Buddha, Bangalore (IN); Partha Hazra, Bangalore (IN); Dinesh Channabasappa Goudar, Bangalore (IN); Srikanth G. Sathyanarayan, Bangalore (IN)

(73) Assignee: BIOCON RESEARCH LIMITED (IN)

( * ) Notice: Subject to any disclaimer, the term of this patent is extended or adjusted under 35 U.S.C. 154(b) by 164 days.

(21) Appl. No.: 15/106,689

(22) PCT Filed: Dec. 22, 2014

(86) PCT No.: PCT/IB2014/067223
§ 371 (c)(1),
(2) Date: Jun. 20, 2016

(87) PCT Pub. No.: WO2015/097643
PCT Pub. Date: Jul. 2, 2015

(65) Prior Publication Data
US 2017/0002052 A1    Jan. 5, 2017

(30) Foreign Application Priority Data
Dec. 23, 2013   (IN) .......................... 6021/CHE/2013

(51) Int. Cl.
| A61K 38/28 | (2006.01) |
| C07K 7/00 | (2006.01) |
| C07K 16/00 | (2006.01) |
| C07K 17/00 | (2006.01) |
| C07K 14/62 | (2006.01) |

(52) U.S. Cl.
CPC .................................. *C07K 14/62* (2013.01)

(58) Field of Classification Search
CPC ............................... A61K 38/28; C07K 14/62
See application file for complete search history.

(56) References Cited

U.S. PATENT DOCUMENTS

| 2,174,862 A | * | 10/1939 | Sahyun | ............... C07K 14/625 530/304 |
| 4,343,898 A | * | 8/1982 | Markussen | ............. C07K 14/62 435/68.1 |
| 4,489,159 A | * | 12/1984 | Markussen | ............. C07K 14/62 435/68.1 |
| 4,601,979 A | * | 7/1986 | Andresen | ............... C07K 14/62 435/68.1 |

FOREIGN PATENT DOCUMENTS

| CN | 102994600 A | * | 3/2013 |
| WO | 83/00504 A1 | | 2/1983 |

* cited by examiner

*Primary Examiner* — Christina Bradley
*Assistant Examiner* — Zachary J Miknis

(57) ABSTRACT

The present invention relates to production of Human Insulin methyl ester by enzymatic reaction. The present invention further relates to production and enhancement of purity of Human Insulin Methyl ester.

19 Claims, 3 Drawing Sheets

40X PH2  40X PH1

40X DF*

40X PH2    40X PH1

40X DF*

60X  40X

40X Ph2

METHOD OF PRODUCTION OF HUMAN INSULIN METHYL ESTER

CROSS-REFERENCE TO RELATED APPLICATIONS

The present application claims the benefit of and the priority to provisional Indian patent application 6021/CHE/2013 filed on 23 Dec. 2013 with the Indian Patent Office. The content of said application filed on 23 Dec. 2013 is incorporated herein by reference for all purposes in its entirety, including an incorporation of any element or part of the description, claims or drawings not contained herein and referred to in Rule 20.5(a) of the PCT, pursuant to Rule 4.18 of the PCT.

TECHNICAL FIELD

The present invention relates to production of Human Insulin methyl ester by enzymatic reaction. The present invention further relates to production and enhancement of purity of Human Insulin Methyl ester.

BACKGROUND OF THE INVENTION

Insulin is a pancreatic hormone involved in the regulation of blood-glucose concentrations. For example, human, porcine, and bovine insulin, insulin analogues and mixed insulins are given to patients with insulin-dependent diabetes mellitus to control their blood-glucose concentrations.

The present invention describes a process related to production of Human Insulin methyl ester by enzymatic reaction. The present invention further relates to production and enhancement of purity of Human Insulin Methyl ester.

STATEMENT OF THE INVENTION

Accordingly, the present invention relates to production of Human Insulin methyl ester by enzymatic reaction; and enhancement of purity of Human Insulin Methyl ester.

BRIEF DESCRIPTION OF THE ACCOMPANYING FIGURES

Figure 1:
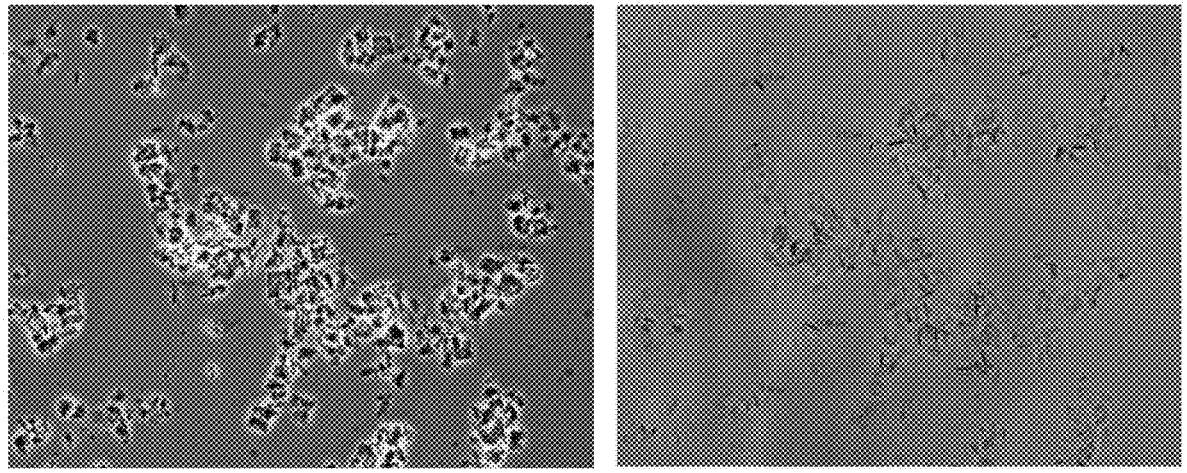
Figure 1:
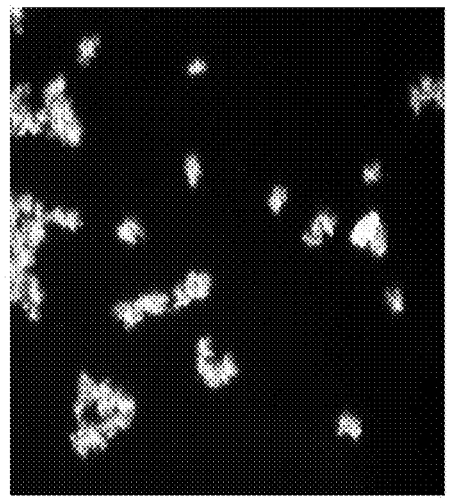

FIG. 1: Shows the microscopic images of Human Insulin precursor microcrystals obtained by crystallization procedure of the instant invention wherein 40×PH2 refers to 40 times magnification using condenser PH2, 40×PH1 refers to 40 times magnification using condenser PH1, and 40×DF* refers to 40 times magnification using dark field mode.

Figure 2:
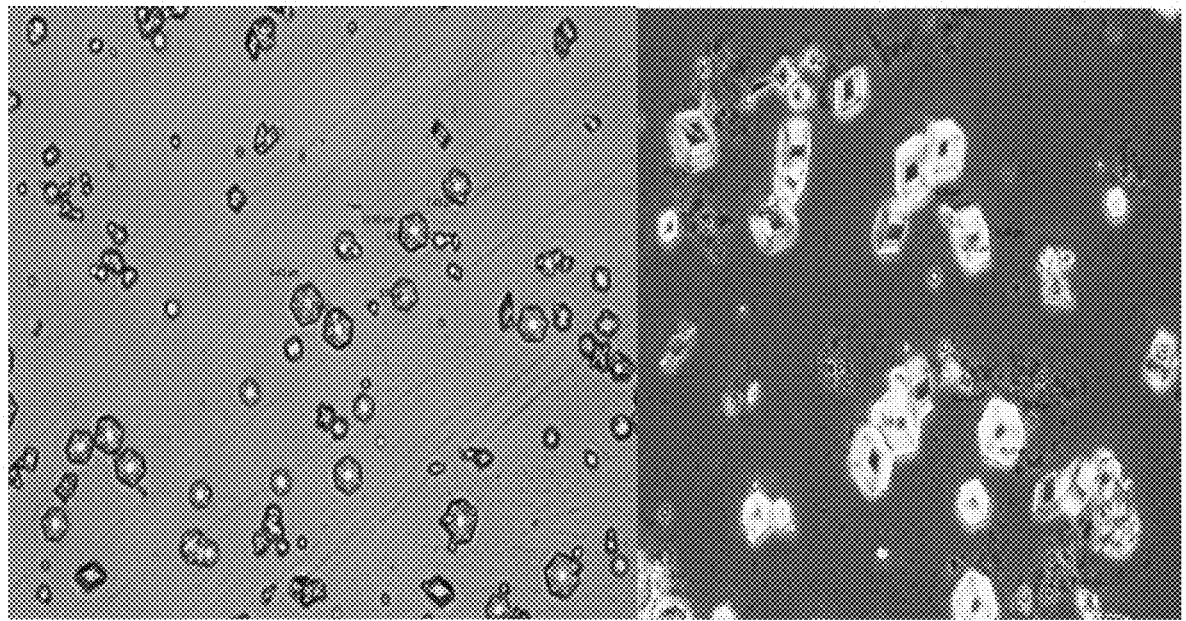
Figure 2:
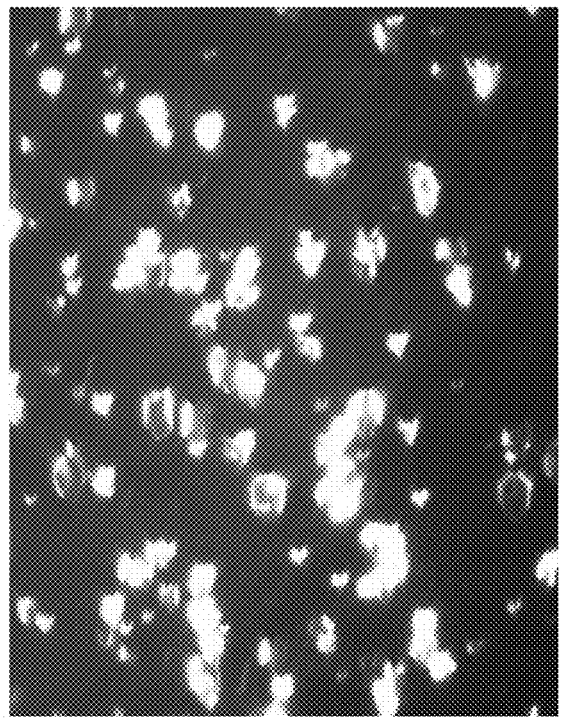

FIG. 2: Shows the microscopic images of Human Insulin methyl ester microcrystals obtained by crystallization procedure of the instant invention wherein 40×PH2 refers to 40 times magnification using condenser PH2, 40×PH1 refers to 40 times magnification using condenser PH1, and 40×DF* refers to 40 times magnification using dark field mode.

Figure 3:
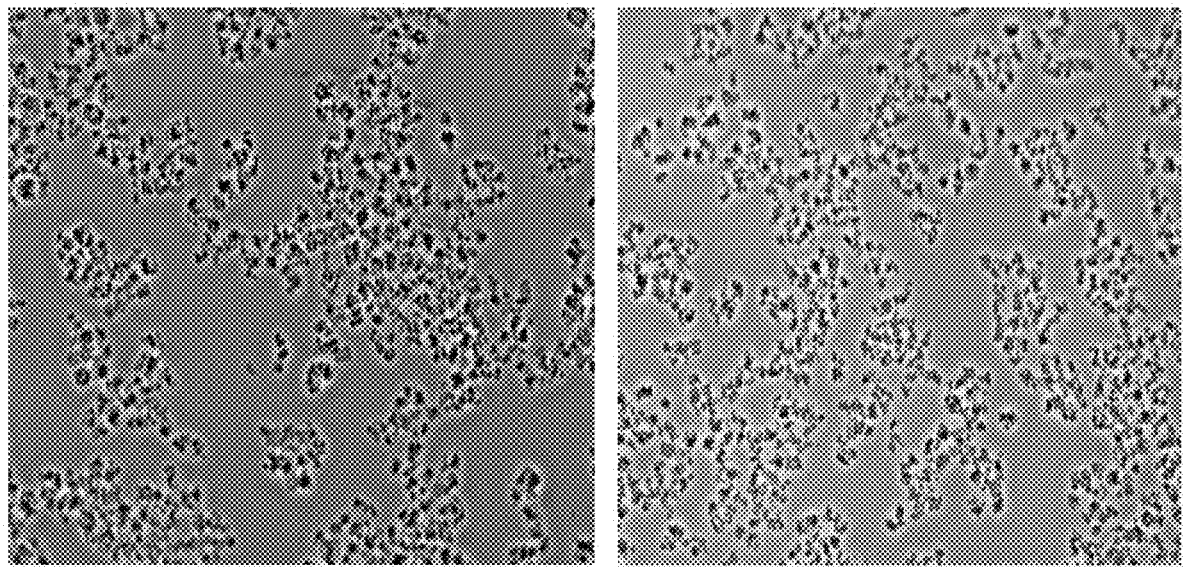

FIG. 3: Shows the microscopic images of Human Insulin precursor microcrystals obtained by crystallization procedure of the instant invention wherein 60× refers to 60 times magnification and 40× refers to 40 times magnification.

Figure 4:
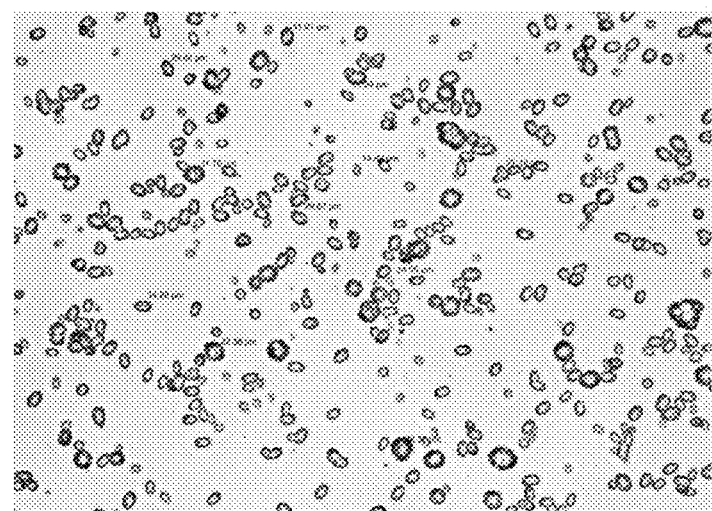

FIG. 4: Shows the microscopic images of Human Insulin methyl ester microcrystals obtained by crystallization procedure of the instant invention wherein 40×Ph2 refers to 40 times magnification using condenser Ph2.

DETAILED DESCRIPTION OF THE INVENTION

The present invention relates to production of Human Insulin methyl ester by enzymatic reaction.

The present invention further relates to production and enhancement in purity of Human Insulin Methyl ester.

In an embodiment of the present invention, dioxane induces cleavage of insulin precursor by trypsin.

In another embodiment, the present invention reduces levels of impurities des B (23-29) and Cyclized form of desB-30 during enzymatic reaction by 40% and 60% respectively.

In yet another embodiment, the present invention enhances purity of Human Insulin Methyl ester by 10% compared to similar process with Dimethyl formamide as reaction solvent.

A more complete understanding can be obtained by reference to the following specific examples, which are provided for purposes of illustration only and are not intended to limit the scope of the invention.

EXAMPLES

Example 1

Step 1:

Human Insulin precursor present in chromatographic elution pool is subjected to crystallization under following conditions to produce needle shaped microcrystals of size between 2-9 µm. Crystallization solution contains human insulin precursor at concentration of 12 g/l, phenol 0.08 ml and 2.1 ml of 4% W/V Zinc chloride solution per gram of human insulin precursor and 1% W/V sodium chloride, and pH of solution adjusted to 4.6 using 2.5N sodium hydroxide and temperature maintained at 22-25° C.

Above crystallization procedure results in a yield of 94%.

Step 2:

Reaction mixture is prepared from crystals obtained in Step 1 to achieve following conditions of human insulin precursor at 80 mg/ml, dioxane solvent at 27.5% V/V, sodium carbonate at 0.1 M, sodium bicarbonate at 0.1M, EDTA 5 mM and trypsin 1400 U/ml and pH is adjusted to 9.5. Reaction mixture is incubated at 25° C. until desB30 conversion of 85% is achieved in 10-16 h.

Similar reported processes targeting desB30 generation from Human Insulin precursor, done with reaction mixture containing 50% V/V DMF, 0.15M tris and trypsin show inferior purity profile at the end of the reaction as depicted in Table 1.

TABLE 1

Reverse Phase Chromatographic Purity profile at the end of hydrolytic reaction.

| Solvent Used | desB30 (%) | DesB (23-29) (%) | Cyclized form of desB30 (%) | Human Insulin Precursor (%) |
|---|---|---|---|---|
| DMF | 74 | 4.5 | 6.0 | 1.5 |
| Dioxane | 85 | 2.3 | 2.3 | 0.4 |

Hence current process with Dioxane, sodium carbonate and sodium bicarbonate salts show enhanced purity of 11% with respect to product desB30.

Step 3:

Thereafter, the above reaction mixture from step 2 is used to generate Human insulin methyl ester by coupling L-threonine methyl ester to desB30.

Coupling reaction mixture is prepared to achieve following conditions, desB30 20 mg/ml, LTME-100 mg/ml, total solvent of 57% V/V composed of Dioxane, DMF and DMSO at 8.2%, 17.0%, 31.8% V/V respectively, Tris 0.15M, trypsin 1400 U/ml and pH is adjusted to 6.6. Reaction mixture is incubated at 25° C. until HIME conversion of greater than 91% is achieved with respect to desB30 in 8-12 h.

Similar reported processes targeting Human Insulin methyl ester generation from desB30, done with reaction mixture containing 57% V/V DMF, 90 mg/ml L-Threonine Methyl Ester and trypsin show inferior purity profile at the end of the reaction as depicted in table 2. Purity profile at the end of above reaction is as follows:

TABLE 2

Reverse Phase Chromatographic Purity profile at the end of coupling reaction.

| Solvent used for step 2 | HIME (%) | desB30 (%) | DesB (23-29) (%) | Cyclized form of desB30 (%) | Precursor (%) |
|---|---|---|---|---|---|
| DMF | 67.0 | 7.0 | 4.5 | 6.0 | 1.5 |
| DMF + DMSO | 77.1 | 6.8 | 2.4 | 2.4 | 0.3 |

Hence current process with DMSO as co-solvent targeting Human Insulin methyl ester (HIME) generation shows enhanced purity of 10% with respect to product desB30, and product related impurities, namely, cyclized form of desB30 and desB (23-29) are reduced by 60% and 40% respectively.

Step 4:

HIME produced according to the step 3 is subjected to crystallization under following conditions to produce rhombohedral crystals of size between 7-15 µm. Crystallization solution contained 22 ml of citrate buffer, 5.5 ml of 4% Zinc chloride solution per gram of HIME and solution pH is adjusted to 6.5 using 1N NaOH and thereafter solution is diluted with purified water to reduce organic solvent concentration to 12.5%, and temperature is maintained at 2-8° C.

Above crystallization procedure shows a yield of 90%.

Purity profile of the crystals obtained by above crystallization procedure shows the reduction in des B (23-29) levels and enhanced purity with respect to Human Insulin methyl ester crystals compared to crystals obtained from DMF based process.

TABLE 3

Reverse Phase Chromatographic Purity profile of Human Insulin methyl ester crystals.

| | Human Insulin Methyl Ester (%) | desB30 (%) | Des B (23-29) (%) | Cyclized form of desB30 | Human Insulin Precursor |
|---|---|---|---|---|---|
| Crystal purity from DMF process | 71 | 7.2 | 0.8 | 5.9 | 1.5 |

TABLE 3-continued

Reverse Phase Chromatographic Purity profile of Human Insulin methyl ester crystals.

| | Human Insulin Methyl Ester (%) | desB30 (%) | Des B (23-29) (%) | Cyclized form of desB30 | Human Insulin Precursor |
|---|---|---|---|---|---|
| Crystal purity from Dioxane + DMF + DMSO process | 80.1 | 7.3 | 0.8 | 2.4 | 0.5 |

Example 2

Human Insulin precursor present in chromatographic elution pool is subjected to crystallization under following conditions to produce 3 dimensional microcrystals of size between 3-6 µm. Crystallization solution contained human insulin precursor at concentration of 12 g/l, phenol 0.08 ml and 2.1 ml of 4% W/V Zinc chloride solution, 11 ml of citrate buffer per gram of human insulin precursor and pH of solution adjusted to 4.6 using 2.5N sodium hydroxide and temperature maintained at 22-25° C.

Above crystallization procedure shows a yield of 94%.

Example 3

HIME produced according to the Example 1, step 3 is subjected to crystallization under following conditions to produce rhombohedral crystals of size between 10-15 µm. Crystallization solution contains 16.5 ml of citrate buffer, 5.0 ml of 4% Zinc chloride solution per gram of HIME and solution pH is adjusted to 6.0 using 1N NaOH and thereafter solution is diluted with purified water to reduce organic solvent concentration to 12.5%, and temperature is maintained at 2-8° C.

Above crystallization procedure shows a yield of 95%.

Example 4

Step 1:

Reaction mixture is prepared from crystals obtained in Step 1 of Example 1 to achieve following conditions, Human insulin precursor at 70 mg/ml, DMF solvent at 40% V/V, sodium carbonate at 0.08 M, sodium bicarbonate at 0.08M, and trypsin 1400 U/ml and pH is adjusted to 9.2. Reaction mixture is incubated at 25° C. until desB30 conversion of 84% is achieved in 10-16 h.

Similar reported processes targeting desB30 generation from Human Insulin precursor, done with reaction mixture containing 50% V/V DMF, 0.15M tris and trypsin show inferior purity profile at the end of the reaction as depicted in Table 4.

TABLE 4

Reverse Phase Chromatographic Purity profile at the end of hydrolytic reaction.

| Solvent Used | desB30 (%) | DesB (23-29) (%) | Cyclized form of desB30 (%) | Human Insulin Precursor (%) |
|---|---|---|---|---|
| DMF + tris | 74 | 4.5 | 6.0 | 1.5 |
| DMF + carbonate | 84 | 3.4 | 2.9 | 1.0 |

Hence current process with DMF, sodium carbonate and sodium bicarbonate salts show enhanced purity of 10% with respect to product desB30.

Step 2:

Thereafter the above reaction mixture from step 1 is used to generate Human insulin methyl ester by coupling L-threonine methyl ester to desB30.

Coupling reaction mixture is prepared to achieve following conditions, desB30 20 mg/ml, LTME-100 mg/ml, DMF at 57% V/V, trypsin 1400 U/ml and pH is adjusted to 6.6. Reaction mixture is incubated at 25° C. until HIME conversion of greater than 91% is achieved with respect to desB30 in 8-12 h.

Similar reported processes targeting Human Insulin methyl ester generation from desB30, done with reaction mixture containing desB30 30 mg/ml, DMF 57% V/V, L-Threonine Methyl Ester 90 mg/ml and trypsin 1400 U/ml show inferior purity profile at the end of the reaction as depicted in table 5.

Purity profile at the end of above reaction is as follows

TABLE 5

Reverse Phase Chromatographic Purity profile at the end of coupling reaction.

| Solvent used for step 2 | HIME (%) | desB30 (%) | DesB (23-29) (%) | Cyclized form of desB30 (%) | Precursor (%) |
|---|---|---|---|---|---|
| DMF + tris | 67.0 | 7.0 | 4.5 | 6.0 | 1.5 |
| DMF + carbonate | 76.0 | 6.8 | 3.8 | 3.0 | 0.8 |

Hence current process with sodium carbonate and sodium bicarbonate as buffering salts with DMF as co-solvent targeting Human Insulin methyl ester generation shows enhanced purity of 9% with respect to product Human Insulin methyl ester, and product related impurities, namely, cyclized form of desB30 and desB (23-29) are reduced by 50% and 19% respectively.

Example 4 explains the role of sodium carbonate and sodium bicarbonate salts in controlling the trypsin from forming cyclized form of desB30.

TABLE 6

Gradient program

| Time (min) | Mobile Phase A (% v/v) | Mobile phase B (% v/v) | Flow Rate (mL/min) |
|---|---|---|---|
| 0.0 | 75 | 25 | 1 |
| 15.0 | 60 | 40 | 1 |
| 16.0 | 25 | 75 | 1 |
| 20.0 | 25 | 75 | 1 |
| 21.0 | 75 | 25 | 1 |
| 25.0 | 75 | 25 | 1 |

Example 5

Step 1:

Reaction mixture was prepared from crystals obtained in Step 1 of Example 1 to achieve following conditions, Human insulin precursor at 70 mg/ml, DMF solvent at 40% V/V, sodium carbonate at 0.08 M, sodium bicarbonate at 0.08M, L-Histidine 0.075M and trypsin 700 U/ml and pH was adjusted to 9.2. Reaction mixture was incubated at 25° C. until desB30 conversion of 84% was achieved in 4-6 h.

Similar process without L-Histidine explained in Example 4 targeting desB30 generation from Human Insulin precursor, shows slower reaction rate and consumes 100% more trypsin.

TABLE 7

Reverse Phase Chromatographic Purity profile* at the end of hydrolytic reaction.

| Solvent + buffering system Used | Reaction time (h) | Trypsin Consumption (U/ml) | desB30 (%) | DesB (23-29) (%) | Cyclized form of desB30 (%) | Human Insulin Precursor (%) |
|---|---|---|---|---|---|---|
| DMF + carbonate | 10-16 | 1400 | 84.0 | 3.4 | 2.2 | 1.0 |
| DMF + carbonate + L-Histidine | 4-6 | 700 | 84.2 | 3.5 | 1.9 | 0.9 |

*Analytical method details

Hence current process with DMF, sodium carbonate, sodium bicarbonate and L-Histidine showed enhanced reaction rate and reduced trypsin consumption by 50% at step 1.

Step 2:

Thereafter the above reaction mixture from step 1 was used to generate Human insulin methyl ester by coupling L-threonine methyl ester to desB30.

Coupling reaction mixture was prepared to achieve following conditions, desB30 30 mg/ml, LTME-90 mg/ml, DMF at 57 V/V, Calcium chloride 5 mM, trypsin 800 U/ml and pH was adjusted to 6.4. Reaction mixture was incubated at 25° C. until HIME conversion of greater than 91% is achieved with respect to desB30 in 8-12 h.

Similar process targeting Human Insulin methyl ester generation from desB30 as explained in example 4 consumes 75% higher trypsin.

Purity profile at the end of above reaction was as follows

TABLE 8

Reverse Phase Chromatographic Purity profile* at the end of coupling reaction.

| Solvent and buffering system used | Reaction time (h) | Trypsin (U/ml) | HIME (%) | desB30 (%) | DesB (23-29) (%) | Cyclized form of desB30 (%) | Precursor (%) |
|---|---|---|---|---|---|---|---|
| DMF + carbonate | 8-12 | 1400 | 76.0 | 6.8 | 3.8 | 2.2 | 0.8 |
| DMF + Carbonate + L-Histidine | 8-12 | 800 | 77.0 | 6.5 | 3.9 | 2.2 | 0.7 |

*Analytical method details

Hence process explained in example 5 with sodium carbonate, sodium bicarbonate and L-Histidine with DMF as co-solvent targeting Human Insulin methyl ester generation showed enhanced reaction rate and reduced overall trypsin consumption by 45%.

Example 5 explains the role of L-Histidine in enhancing the overall reaction rate.

Example 6

Reaction mixture was prepared from crystals obtained in Step 1 of Example 1 to achieve following conditions, Human insulin precursor at 80 mg/ml, t-butanol at 25% V/V, sodium carbonate at 0.1 M, sodium bicarbonate at 0.1M, and trypsin 700 U/ml and pH was adjusted to 9.2. Reaction mixture was incubated at 25° C. until desB30 conversion of 86% was achieved in 4-6 h.

Hence current process using t-butanol as a reaction solvent shows 73% lower cyclized form of desB30 compared to DMF as explained in step 1 of example 5.

Purity profile at the end of above reaction was as follows

TABLE 9

Reverse Phase Chromatographic Purity profile* at the end of hydrolytic reaction.

| Solvent + buffering system Used | Reaction time (h) | Trypsin Consumption (U/ml) | desB30 (%) | DesB (23-29) (%) | Cyclized form of desB30 (%) | Human Insulin Precursor (%) |
|---|---|---|---|---|---|---|
| t-butanol + carbonate | 4-6 | 700 | 86.0 | 2.5 | 0.5 | 1.0 |
| DMF + carbonate | 4-6 | 700 | 84.2 | 3.5 | 1.9 | 0.9 |

*Analytical method details

Analytical Method Details:
Equipment
  Analytical HPLC system
  ACE C18, 5 μm, 4.6×250 mm
Mobile Phases used
Mobile phase A:
  0.1% V/V Trifluoroacetic acid in water Pipette out 1 mL of Trifluoro acetic acid in a measuring cylinder and make up the volume to 1000 mL with purified water. Sonicate the mixture for 5 minutes.
Mobile phase B:
  100% Acetonitrile (HPLC grade)
Chromatography Conditions:
  Column: ACE 300-C18, 5 μm; 4.6×250 mm (Waters)
  Column temperature: 40° C.
  Vial chamber temperature: 4° C.
  Wavelength monitored: 220 nm
  Injection Volume (Std.): 10 μL
  Assay Time: 25 min.

TABLE 10

Gradient program

| Time (min) | Mobile Phase A (% v/v) | Mobile phase B (% v/v) | Flow Rate (mL/min) |
|---|---|---|---|
| 0.0 | 75 | 25 | 1 |
| 15.0 | 60 | 40 | 1 |
| 16.0 | 25 | 75 | 1 |
| 20.0 | 25 | 75 | 1 |
| 21.0 | 75 | 25 | 1 |
| 25.0 | 75 | 25 | 1 |

What is claimed is:

1. A method of obtaining a human insulin methyl ester, the method comprising contacting, in the presence of trypsin, insulin desB30 with L-threonine methyl ester in a solvent, the solvent comprising water, dimethyl sulfoxide and dimethylformamide in a ratio of water/dimethyl sulfoxide from about 1:1 (v/v) to about 1:0.5 (v/v), and a ratio of water/dimethylformamide from about 1:0.6 (v/v) to about 1:0.3 (v/v); and wherein the solvent further comprises dioxane, wherein dioxane is present in the solvent in a ratio of water/dioxane of about 1:0.2 (v/v) or less.

2. The method of claim 1, wherein the ratio of water/dimethyl sulfoxide in the solvent is from about 1:0.8 (v/v) to about 1:0.7 (v/v), and the ratio of water/dimethylformamide is from about 1:0.45 (v/v) to about 1:0.35 (v/v).

3. The method of claim 1, wherein the ratio of water/dimethyl sulfoxide in the solvent is about 1:0.74 (v/v), the ratio of water/dimethylformamide is about 1:0.4 (v/v), and the ratio of water/dioxane is about 1:0.19 (v/v).

4. The method of claim 1, wherein the solvent contains tris(hydroxymethyl)aminomethane (Tris).

5. The method of claim 1, wherein the solvent comprises in an amount from about 0.03 to about 0.3 M at least one selected from the group consisting of carbonate salt, sodium carbonate, potassium carbonate, bicarbonate salt, sodium hydrogen carbonate, and potassium hydrogen carbonate, or a hydrate thereof.

6. The method of claim 1, wherein desB30 is obtained from at least one selected from the group consisting of (a) a precursor insulin, and (b) human preproinsulin.

7. The method of claim 6, wherein desB30 is obtained by contacting the precursor insulin with trypsin in a buffer of about 0.05M to 0.125M histidine comprising at least one selected from the group of (a) water and dioxane in a ratio of water/dioxane from about 1:0.5 (v/v) to about 1:0.3 (v/v); and (b) water and dimethylformamide in a ratio of water/dimethylformamide from about 1:0.9 (v/v) to about 1:0.3 (v/v).

8. The method of claim 7, wherein the solvent in obtaining desB30 further comprises a carbonate and/or a bicarbonate salt in an amount of about 0.05 to about 0.3 M.

9. The method of claim 7, wherein the solvent in obtaining desB30 does not contain tris(hydroxymethyl)aminomethane (Tris).

10. The method of claim 1, wherein contacting desB30 with L-threonine methyl ester is carried out in the presence of trypsin at an amount selected from the group consisting of about 20 U or more trypsin per mg of desB30, and about 50 U or more trypsin per mg of desB30.

11. The method of claim 1, wherein contacting desB30 with L-threonine methyl ester is carried out at a pH in the range from about 6.0 to about 7.5.

12. The method of claim 1, further comprising collecting the produced human insulin methyl ester after a period of 7 hours or more at a temperature from about 18° C. to about 30° C.

13. The method of claim 12, comprising crystallising the produced human insulin methyl ester by adding citrate buffer and zinc chloride, and maintaining the solution at about 12° C. or less.

14. The method of claim 13, wherein crystallising the produced human insulin methyl ester comprises, after adding citrate and zinc chloride, diluting the solvent with water to an organic solvent concentration of about 13% or less.

15. The method of claim 7, wherein the buffer in obtaining desB30 has a pH in the range from about 8.5 to about 10.0.

16. The method of claim 7, wherein contacting desB30 with L-threonine methyl ester is carried out in the presence of trypsin at an amount selected from the group consisting of about 10 U or more trypsin per mg desB30, and about 20 U or more trypsin per mg of the precursor insulin.

17. The method of claim 12, wherein the temperature is about 25° C.

18. The method of claim 13, wherein the amount of zinc chloride is selected from the group consisting of about 0.5 mmol to about 5 mmol per gram of human insulin methyl ester, and about 1 mmol to about 2 mmol zinc chloride per gram of human insulin methyl ester.

19. The method of claim 13, wherein the citrate buffer comprises 0.02 to 0.06 molar citric acid and 0.2 to 0.6 molar disodium hydrogen orthophosphate.

\* \* \* \* \*